United States Patent
Teves

(10) Patent No.: US 7,210,959 B1
(45) Date of Patent: May 1, 2007

(54) APPARATUS FOR MAINTAINING OXIMETER CABLES IN ORDERLY CONDITION

(76) Inventor: Leonides Y. Teves, 1607 54th St. West, Bradenton, FL (US) 34209

( * ) Notice: Subject to any disclaimer, the term of this patent is extended or adjusted under 35 U.S.C. 154(b) by 0 days.

(21) Appl. No.: 11/237,247

(22) Filed: Sep. 28, 2005

(51) Int. Cl.
*H01R 13/72* (2006.01)

(52) U.S. Cl. .......................... 439/501; 439/505
(58) Field of Classification Search ........ 439/501–502, 439/505
See application file for complete search history.

(56) References Cited

U.S. PATENT DOCUMENTS

| | | | | |
|---|---|---|---|---|
| 3,272,277 | A * | 9/1966 | Budzich | 180/243 |
| 4,648,682 | A * | 3/1987 | Tubbs | 439/391 |
| 5,850,440 | A * | 12/1998 | Hannon et al. | 379/446 |
| 6,056,591 | A * | 5/2000 | Liao | 439/501 |
| 6,500,025 | B1 * | 12/2002 | Moenkhaus et al. | 439/502 |

* cited by examiner

*Primary Examiner*—Truc Nguyen
(74) *Attorney, Agent, or Firm*—Ronald E. Smith

(57) ABSTRACT

An oximeter machine includes a built in first socket that is positively engaged by a jack at the proximal end of a first cable. The distal end of the first cable includes a jack that engages the proximal end of a second socket. The proximal end of a second, adjustable length cable engages the distal end of the second socket and the distal end of the second cable engages the proximal end of a third socket. The proximal end of a third cable engages the distal end of the third socket and the distal end of the third cable is engaged to an oximeter finger sensor. A retractable cable housing enables the length of the second cable to be adjusted so that its length may be minimized to reduce cable tangling and to minimize a tripping hazard.

1 Claim, 1 Drawing Sheet

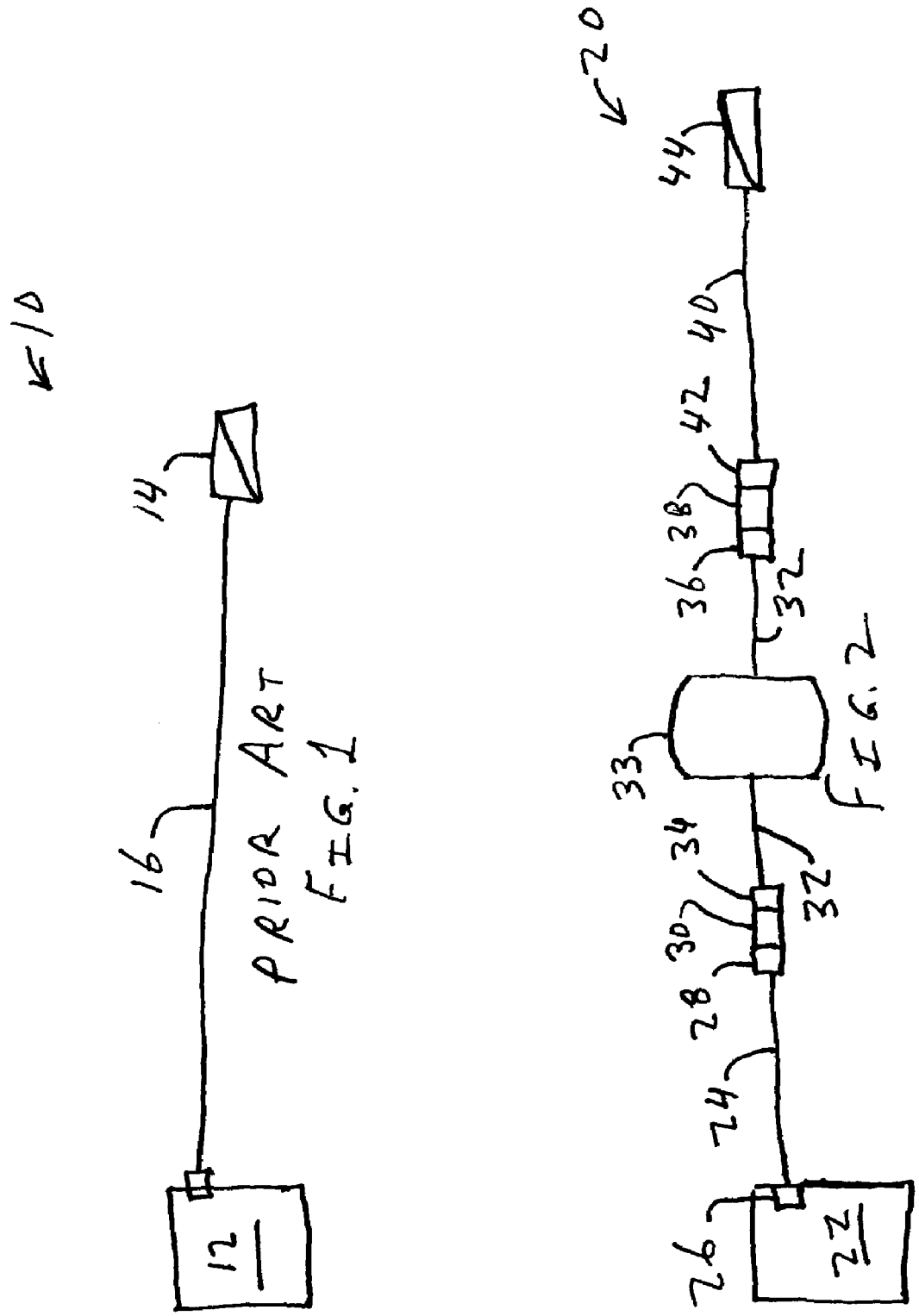

APPARATUS FOR MAINTAINING OXIMETER CABLES IN ORDERLY CONDITION

BACKGROUND OF THE INVENTION

1. Field of the Invention

This invention relates, generally, to oximeter machines and to combination oximeter/EKG machines. More particularly, it relates to a structure and method for preventing oximeter cables from getting into a disorderly condition.

2. Description of the Prior Art

Oximeter cables are lengthy. They extend from an oximeter machine or a combination oximeter/EKG machine to an oximeter finger sensor. A patient inserts a finger into the oximeter finger sensor.

The cables are long because oximeter machines (or combination oximeter/EKG machines) are often used in operating rooms where the machine must be positioned a substantial distance from a patient. As a result, the cables often wind up on the floor, walked upon by the members of a surgical team. The connection between the machine and the cable, at the proximal end of the cable, is easily broken when the cable is pulled. Thus, whenever someone trips over a cable and yanks it from the machine, the connection must be restored. The oximeter cable may also become tangled with other cables attached to other machines, or it may become tangled with itself or other items in the operating room.

What is needed, then, is an apparatus and method for keeping elongate oximeter cables in an untangled, orderly condition during use. A need also exists for an oximeter cable that is not easily separated from an oximeter/EKG machine.

However, in view of the prior art taken as a whole at the time the present invention was made, it was not obvious to those of ordinary skill how the identified needs could be fulfilled.

SUMMARY OF THE INVENTION

The long-standing but heretofore unfulfilled need for a means for maintaining oximeter cables in an orderly, untangled condition is now met by a new, useful, and non-obvious invention.

The novel structure adds an RJ45 or similar jack to the proximal end of an oximeter cable. It also modifies an oximeter machine or a combination oximeter/EKG machine by adding an RJ45 socket, or other registered jack socket or other quick release means, to such oximeter machine or to a combination oximeter/EKG machine. This enables connection of a first jack at the proximal end of an oximeter cable to said machine socket. This prevents the proximal end of the improved oximeter cable from being yanked inadvertently from the machine. The oximeter machine socket is hereinafter referred to as the first socket.

A second RJ45 or similar jack is provided at the distal end of the oximeter cable and said second RJ45 jack is releasably engaged to a second RJ45 or similar socket.

A retractable, adjustable length cable has an RJ45 jack or similar jack at its opposite ends. The proximal end of the retractable cable releasably engages the second socket. The distal end of the retractable cable engages a third RJ45 or similar socket.

A standard cable having an RJ45 or similar jack at its proximal end releasably engages the third socket and the distal end of the standard cable extends to an oximeter finger sensor.

The retractable cable is adjustable over a wide range of lengths. This feature of the retractable cable minimizes the length of the cable assembly and thus minimizes the tripping hazard. The use of RJ45 or similar jacks and sockets throughout the cable assembly enables the assembly to be quickly and easily installed or removed as needed.

The oximeter, retractable, and standard cables are herein referred to as the first, second, and third cables.

More particularly, the novel cable assembly for interconnecting an oximeter machine to an oximeter finger sensor includes an oximeter machine having a first socket built thereinto, and a first cable having a jack formed in a proximal and a distal end thereof. The jack at the proximal end of the first cable is adapted to releasably engage the first socket.

The novel assembly further includes a second socket, said second socket being provided in the form of a double socket having a proximal socket and a distal socket. The jack at the distal end of the first cable is adapted to releasably engage the proximal socket of the second socket.

A second cable includes a retractable cable housing and has a jack at its proximal end and a jack at its distal end. The jack at the proximal end of the second cable is adapted to releasably engage a distal end of the second socket.

The novel assembly further includes a third socket, said third socket being provided in the form of a double socket having a proximal socket and a distal socket. The jack at the distal end of the second cable is adapted to releasably engage the proximal socket of the third socket.

A third cable has a jack at a proximal end and an oximeter finger sensor at its distal end. The jack at the proximal end of the third cable is adapted to releasably engage the distal socket of the third socket.

The retractable cable housing adjustably minimizes the length of the second cable when the oximeter finger sensor and oximeter machine are interconnected to one another and therefore allows the respective lengths of the first and third cables.

These and other advantages will become apparent as this disclosure proceeds. The invention includes the features of construction, arrangement of parts, and combination of elements set forth herein, and the scope of the invention is set forth in the claims appended hereto.

BRIEF DESCRIPTION OF THE DRAWINGS

For a fuller understanding of the nature and objects of the invention, reference should be made to the following detailed description, taken in connection with the accompanying drawings, in which:

FIG. 1 is a diagrammatic view of a prior art oximeter machine and an oximeter finger sensor connected to one another by a prior art cable; and FIG. 2 is a diagrammatic view of the novel structure that includes a retractable cable.

DETAILED DESCRIPTION OF THE PREFERRED EMBODIMENT

Referring first to FIG. 1, it will there be seen that a prior art oximeter machine and its related parts are denoted by the reference numeral 10 as a whole. Machine 12 is an oximeter machine or a combination oximeter/EKG machine. Finger sensor 14 is connected to machine 12 by elongate cable 16. The proximal end of cable 16 includes a cylindrical connector that slidingly engages a mating cylindrical connector formed in machine 10. Such connection is easily overcome if cable 16 is pulled upon. Moreover, elongate cable 18 has a fixed length. It can become easily tangled with other cables in the room and it represents a tripping hazard.

Referring now to FIG. 2, it will there be seen that an illustrative embodiment of the invention is denoted as a whole by the reference numeral 20.

Machine 22 is an oximeter machine or a combination oximeter/EKG machine. An RJ45 or similar socket is built into said machine 22, said socket hereinafter being referred to as the first socket.

Oximeter cable 24, also referred to herein as the first cable, has an RJ45 or similar jack at each of its opposite ends. Jack 26 at the proximal end of said first cable is adapted to releasably engage the first socket in a well-known way, thereby overcoming the separation problem associated with the prior art cylindrical jack and socket because an RJ45 jack and its socket are not separable by a pulling force alone.

Second socket 30 is a double socket, having a proximal socket and a distal socket. Jack 28 at the distal end of oximeter cable 24 is adapted to releasably engage the proximal end of second socket 30, which is also of the RJ45 or similar type.

Retractable cable 32, also referred to herein as the second cable, has RJ45 or similar jacks 34, 36 at its opposite ends. Proximal jack 34 is adapted to releasably engage the distal socket of second socket 30 and distal jack 36 is adapted to releasably engage the proximal socket of third double socket 38.

Retractable cable 32 extends from opposite ends of retractable cable housing 33. The retractable cable housing is described in copending U.S. patent application Ser. No. 10/708,534, filed by the present inventor on Mar. 10, 2004. Said disclosure is hereby incorporated by reference into this disclosure.

Standard cable 40, also referred to herein as the third cable, has a RJ45 or similar jack 42 at its proximal end that is adapted to releasably engage the distal socket of third socket 38. The distal end of standard cable 40 is attached to oximeter finger sensor 44 in a conventional way.

The use of RJ45 sockets and jacks throughout the novel structure prevents inadvertent disconnections between the various parts of the assembly but enables quick and easy assembly or disconnection. Retractable cable housing 33 enables second cable 32 to always be extended by a minimum length to minimize tangling with other cables and to minimize the tripping hazard. Said retractable cable housing also enables first or oximeter cable 24 and third or standard cable 40 to have minimum lengths.

It will thus be seen that the objects set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described,

What is claimed is:

1. A cable assembly for interconnecting an oximeter machine to an oximeter finger sensor, comprising:
   an oximeter machine having a first socket built thereinto;
   a first fixed-length cable having a jack formed in a proximal and a distal end thereof;
   said jack at said proximal end of said first cable adapted to releasably engage said first socket;
   a second socket, said second socket being a double socket having a proximal socket and a distal socket;
   said jack at said distal end of said first cable adapted to releasably engage said proximal end of said second socket;
   a second adjustable-length cable including a retractable cable housing, said second cable having a jack at its proximal end and a jack at its distal end;
   said jack at said proximal end of said second cable adapted to releasably engage a distal end of said second socket;
   a third socket, said third socket being a double socket having a proximal socket and a distal socket;
   said jack at said distal end of said second cable adapted to releasably engage said proximal socket of said third socket;
   a third fixed-length cable having a jack at a proximal end and an oximeter finger sensor at its distal end;
   said jack at said proximal end of said third cable adapted to releasably engage said distal socket of said third socket;
   whereby said retractable cable housing minimizes the length of said second adjustable-length cable when said oximeter finger sensor and oximeter machine are interconnected to one another.

\* \* \* \* \*